United States Patent
Miersch

(10) Patent No.: US 12,366,296 B2
(45) Date of Patent: Jul. 22, 2025

(54) STOPCOCK, PLUG FOR A STOPCOCK, AND METHOD FOR PRODUCING A PLUG FOR A STOPCOCK

(71) Applicant: Olympus Winter & Ibe GmbH, Hamburg (DE)

(72) Inventor: Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 17/711,350

(22) Filed: Apr. 1, 2022

(65) Prior Publication Data
US 2022/0316604 A1 Oct. 6, 2022

(30) Foreign Application Priority Data
Apr. 1, 2021 (DE) .................. 10 2021 108 314.1

(51) Int. Cl.
*F16K 5/02* (2006.01)
*A61B 1/015* (2006.01)
*F16K 31/60* (2006.01)

(52) U.S. Cl.
CPC ............ *F16K 5/0207* (2013.01); *A61B 1/015* (2013.01); *F16K 5/0278* (2013.01); *F16K 31/602* (2013.01)

(58) Field of Classification Search
CPC ........ F16K 5/0207; F16K 5/0278; F16K 5/02; F16K 5/16; F16K 31/602; A61B 1/015; A61B 1/00137; A61B 1/00068; A61B 1/00064; A61B 1/00131; A61B 1/00195; A61B 1/018; A61M 39/22; A61M 2039/229

See application file for complete search history.

(56) References Cited

U.S. PATENT DOCUMENTS

| | | | | |
|---|---|---|---|---|
| 684,399 A | * | 10/1901 | Ashley | F16K 5/02 137/246.23 |
| 2,045,113 A | * | 6/1936 | Ward | F16K 5/162 251/312 |
| 2,898,081 A | * | 8/1959 | Johnson | F16K 35/10 411/530 |

(Continued)

FOREIGN PATENT DOCUMENTS

| | | |
|---|---|---|
| DE | 44 15 284 A1 | 11/1995 |
| DE | 102019112594 A1 | 11/2020 |

(Continued)

*Primary Examiner* — Craig M Schneider
*Assistant Examiner* — Andrew J Rost
(74) *Attorney, Agent, or Firm* — Oliff PLC

(57) ABSTRACT

In order to flush away local bleeding during surgery with a medical instrument, the instruments are commonly provided with a flushing device. In order to be able to control an inflow and outflow of a flushing liquid, the instruments have a stopcock. In order to achieve the sealing action of the stopcock, the plugs of the stopcock have to be formed with a very high degree of precision. The known production processes for such plugs are very cumbersome and cost-intensive. This provides a plug for a stopcock and a stopcock and a method for producing a plug, by way of which the stated problem is eliminated. This is achieved in that a plug, with a grip part and a cone part, is formed in one part and can be produced in a single process step.

8 Claims, 3 Drawing Sheets

(56) References Cited

U.S. PATENT DOCUMENTS

| | | | | |
|---|---|---|---|---|
| 3,052,581 | A * | 9/1962 | Gutknecht | B44C 3/042 |
| | | | | 264/251 |
| 3,806,087 | A * | 4/1974 | Hulslander | F16K 5/166 |
| | | | | 251/315.01 |
| 4,572,231 | A * | 2/1986 | Katayama | F16K 5/22 |
| | | | | 251/317 |
| 4,844,413 | A * | 7/1989 | Weber | F16K 5/0478 |
| | | | | 251/314 |
| 5,947,443 | A * | 9/1999 | Shellenbarger | F16K 5/0478 |
| | | | | 251/181 |
| 6,585,003 | B2 * | 7/2003 | Steiner | F16K 5/0242 |
| | | | | 251/230 |
| 7,204,474 | B2 * | 4/2007 | McGuire | F16K 5/184 |
| | | | | 251/309 |
| 8,602,058 | B1 * | 12/2013 | Del Castillo | F16K 31/52466 |
| | | | | 251/227 |
| 2016/0143516 | A1 | 5/2016 | Xu et al. | |
| 2017/0363220 | A1 * | 12/2017 | Yan | F16K 11/085 |
| 2020/0352415 | A1 | 11/2020 | Harris et al. | |

FOREIGN PATENT DOCUMENTS

| | | |
|---|---|---|
| DE | 10 2019 124 638 A1 | 3/2021 |
| WO | 2016165806 A1 | 10/2016 |

\* cited by examiner

STOPCOCK, PLUG FOR A STOPCOCK, AND METHOD FOR PRODUCING A PLUG FOR A STOPCOCK

The invention relates to a plug for of a stopcock. The invention furthermore relates to a stopcock. Finally, the invention also relates to a method for producing a plug for a stopcock.

Medical instruments, such as for example endoscopes, commonly have an elongate, tubular shaft and an optical unit, which are used for examination of interior spaces of the human body and for minimally invasive surgery. Passage instruments, such as stone-collecting baskets, instruments for electrosurgical resection or forceps, can be guided to the surgical site through the shaft section of the instrument. In order to flush away local bleeding which occurs during surgery and to protect tissue for example from heat damage due to a high-frequency electrosurgical application, the instruments are commonly provided with a flushing device which permanently flushes around the tissue which is situated in front of the distal shaft end. The flushing liquid can be guided through an inner tube or through an outer tube of the instrument by way of corresponding separate liquid channels. In order to be able to control the inflow and outflow of the liquid, the liquid channels generally have a stopcock in their proximal end region. Corresponding stopcocks are described for example in DE 10 2014 002 158 B4 and DE 10 2016 011 184 A1.

The stopcocks commonly consist of a housing and a plug which is mounted rotatably therein. The housing generally has a cuboidal or cylindrical basic shape with an interior space. Said interior space can be connected via two connection parts to a liquid channel of the instrument and also to for example a supply line of a pump or the like. In said in particular conical interior space, the plug can be fixed rotatably. The plug consists of a cone part with a cone surface, wherein the shape of the cone part corresponds substantially to the shape of the interior space of the housing. The plug furthermore has a grip part with a grip. Via said grip, which is connected to the cone part, the plug can be rotated about an axis of rotation. The cone part is passed through by a bore which generally extends perpendicularly to the axis of rotation. In terms of its dimensions and in terms of its orientation, said bore corresponds to the openings of the two connection parts in the housing. By rotation of the plug about the axis of rotation, the two openings of the bore can be brought into line with the openings of the two connection parts of the housing, so that a continuous channel through the stopcock is formed. By a further corresponding rotation of the plug, the bore can be brought to a position in which the continuous channel or the fluid channel is interrupted. In both positions, it is essential for the functional capability of the stopcock that the fluid flows only through the channel and not between the cone surface and the inner wall of the housing or that no fluid flows through the stopcock.

For this sealing action of the stopcock or for the channeling of the fluid, the cone surface of the plug has webs. Said webs are arranged as projections on the cone surface and are formed in such a way that they provide sealing closure with the inner wall of the housing. For this purpose, the cone part may be assigned two annular webs above and below the bore. Due to the conical shape of the cone part, said annular webs have different diameters. Furthermore, on the cone surface, there may be formed vertical webs which are arranged at the side of the openings of the bore and which extend from one annular web to the other annular web.

In order to achieve the sealing action of the stopcock, these webs must be formed or produced with a very high degree of precision and, furthermore, need a high material hardness for corresponding durability. Generally, the plugs are produced from wear-resistant and dimensionally stable materials, such as for example PEEK. In order to achieve the degree of precision of the sealing surfaces, the PEEK material is machined in a turning process. Said turning process is realized at the PEEK semi-finished material or after the PEEK component or the cone part of the plug has been produced in a preceding injection-moulding process. After the sealing surfaces of the cone part have acquired the sufficient degree of precision by way of the turning process, the grip part of the plug is bonded adhesively to cone part of the plug in a further process step. Subsequently, the multipart plug, which is produced by multiple process steps, has to be thoroughly cleaned.

If the plug is injection-moulded together with the grip, it is necessary for the finished injection-moulded plug, after the injection moulding, to be received in a further machine for turning. Only by way of this further process step of turning is the sufficient degree of precision of the sealing surfaces of the webs achieved. Both production processes outlined here for a plug for a stopcock are very cumbersome and cost-intensive.

Proceeding from this, the problem addressed by the present invention is that of providing a plug for a stopcock and also a stopcock and a method for producing a plug, by way of which the stated problems are eliminated.

A solution to the stated problem is described. Accordingly, it is provided that the plug, with the grip part and the cone part, is formed in one part and can be produced in a single process step. Consequently, firstly the production is particularly simple and inexpensive, and secondly the plug achieves exceptional stability as a result. As a result of this one-part design, there is no need for the grip part and the cone part to be bonded together adhesively in a further process step. Rather, this plug consists of a single integral part.

Preferably, it is furthermore provided according to the invention that a cone surface of the cone part has at least two horizontal webs which extend annularly around the cone part, wherein one web is arranged above and one web is arranged below a bore through the cone part. It may furthermore be provided that the cone surface has at least four vertical webs which extend, in each case adjacent to outlet openings of the bore, along the cone surface, wherein the vertical webs are of straight or curved form and are arranged in particular semicircularly around the bore. Here, the ends of the vertical webs coincide in each case with the horizontal webs. These webs on the cone surface of the plug allow a sufficiently high degree of sealing between the plug and the housing to be produced. Here, however, it is important that sealing surfaces of the webs have the required degree of precision. The one-part plugs claimed herein have precisely such webs. In particular by way of the claimed production method, production of webs which have an exceptional hardness and are thus formed to be durable and with very high precision, and thus produce a sealed connection with respect to an inner wall of the housing, is possible.

It is also conceivable that the vertical webs have a width which corresponds at least to the diameter of the bore. In this way, a slight rotation is enough to bring the plug to a closed position.

In particular, it is provided that the cone part, the grip part and the webs are produced in one part from the same material, specifically PEEK. This material can be injection-moulded particularly well, on the one hand, and can be embossed, on the other hand. The combination of the injection-moulding process and the embossing process makes it possible for the one-part plug having the above-described required properties to be produced. Furthermore, it is also conceivable for the plug to be produced from a different but comparable material.

It may furthermore be provided according to the invention that the form of at least the vertical webs, in particular of all the webs, has a particularly high degree of precision as a result of the embossing process. During the embossing process, the vertical annular webs are embossed in such a way that their outer circumference is reduced. This multi-dimensional embossing allows the webs of the plug to be processed precisely in such a way that they have the required degree of precision and hardness.

A stopcock for solving the problem stated at the outset has the features described herein. Accordingly, it is provided that said stopcock, for producing and breaking a fluidic connection between at least two connection parts and has a plug.

A method for solving the problem is described. Accordingly, it is provided that the plug, with the cone part and the grip part, is produced in one part. As a result of this one-part production or as a result of the reduction of the production to one fundamental production process, the entire production can be simplified and made less expensive than with the conventional methods.

A particularly advantageous exemplary embodiment of the invention consists in that the plug, with the cone part and the grip part, is injection-moulded in one part, preferably from PEEK, and is embossed in a directly following process. As a result of the embossing, the cone surface and/or the webs acquire(s) the required degree of precision. Here, according to the invention, the embossing process is realized in the apparatus for the injection moulding. Konzelmann GmbH already produces sealing rings composed of a high-performance plastic, where the injection-moulding process is followed directly by the embossing process for producing the required degree of precision of the sealing rings in a plane for the sealing. Through the method described here, this one-dimensional principle is carried over to the cone part of the plug into multiple dimensions. This method, which comprises both injection moulding and embossing, allows simple and quick production of a plug which has the required degree of precision. Re-clamping of the plug in an embossing apparatus or subsequent adhesive bonding of the individual constituent parts of the plug is dispensed with, whereby the entire process is made particularly inexpensive. Furthermore, it is conceivable that, by way of a multiple injection-moulding process in combination with the embossing, a multiplicity of plugs is produced in a simultaneous manner.

Preferably, the webs or the sealing surfaces of the webs are flattened during the embossing process. As a result of this flattening, the webs acquire the required hardness and degree of precision for obtaining, together with the inner wall of the housing, the required sealing.

One possible exemplary embodiment of the invention is illustrated schematically in the drawing. In the drawing.

Figure 1:
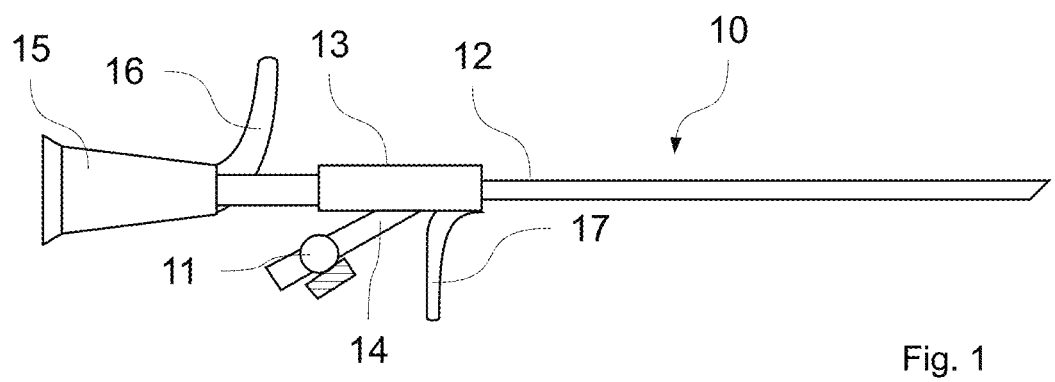
FIG. 1 shows a schematic side view of an endoscope with a stopcock.

FIG. 1 highly schematically illustrates an endoscope 10. Said endoscope 10 has a stopcock 11. A liquid channel (not visible here) runs within a shaft part 12 of the endoscope 10 and passes, angled, by way of a main body 13, to an inlet connector 14. The stopcock 11 is arranged on the inlet connector 14 for the purpose of regulating the liquid flow through the liquid channel. A pump for feeding liquid into the liquid channel, for example, may be connected to the inlet connector 14.

The side view illustrated here shows the medical endoscope 10 in the orientation in which it is normally used during an operation. The endoscope 10 has at its proximal end an eyepiece 15 for observation of the operation area. In order for the operator to be able to securely hold the endoscope 10 during the operation, two grip pieces 16, 17 are fastened to the endoscope 10. The grip pieces 16, 17 are normally formed ergonomically in such a way that the operator can hold the endoscope 10 in one hand with the aid of the grip pieces 16, 17. The operator correspondingly has the other hand free in order, for example, to introduce passage instruments into a work channel of the instrument and to operate them.

Figure 2:
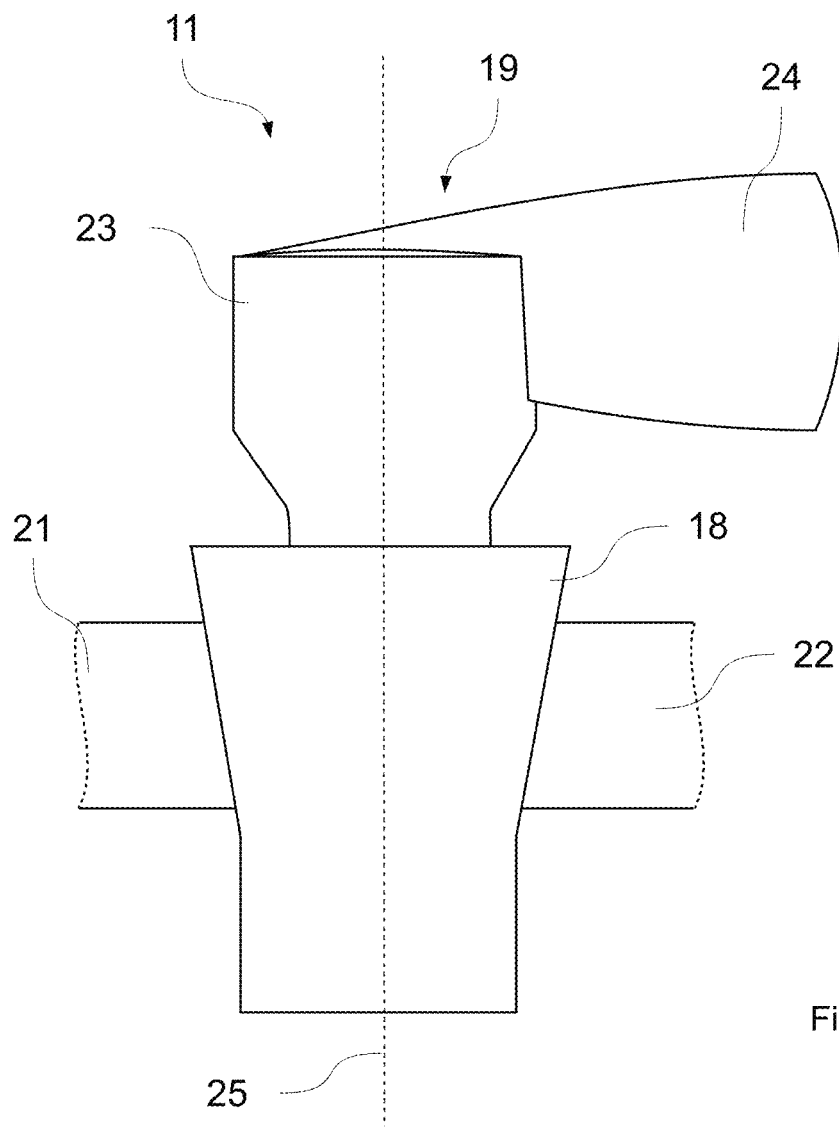
FIG. 2 shows a schematic side view of a stopcock.

FIG. 2 highly schematically illustrates one possible exemplary embodiment of the stopcock 11 according to the invention. Said stopcock 11 has a housing 18 and a plug 19, the cone part 20 of which plug is received in the housing 18. The housing 18 has two connection parts 21, 22, by way of which it can be coupled to the inlet connector 14 of the endoscope 10. It is also possible for connecting parts, such as further valves or the like, to be assigned to said two connection parts 21, 22.

As can be seen in FIGS. 2 to 5, above the cone part 20 along an axis of rotation 25 of the stopcock 11, the plug 19 has a grip 23 which comprises a grip part 24. The grip part 24 may, for this purpose, be ergonomically formed, so as to facilitate holding and movement by the user.

According to the invention, the plug 19 is formed in one part, that is to say the cone part 20 and the grip 23 form an integral constituent part of the plug 19. Consequently, the plug 19 described here proves to be advantageous in comparison with the known plugs since it is not assemblable from multiple constituent parts by way of for example adhesive bonding. On the one hand, this reduces the outlay in terms of assembly, and, on the other hand, the one-part design increases the stability of the plug 19.

By actuation of the grip 23 or by rotation of the plug 19 about the axis of rotation 25, a fluidic connection can be opened up or broken by the stopcock 11. For this purpose, the cone part 20 has a bore 26 which extends through the entire cone part 20 perpendicularly to the axis of rotation 25. The bore 26 has two openings 28, 29, which are situated in a cone surface 27 of the cone part 20. In the open position of the stopcock 11, the openings 28, 29 of the plug 19 are situated congruently together with the tubular connection parts 21, 22 of the housing 18. For the separation of the fluid channel, the plug 19 is rotated about the axis of rotation 25 in such a way that the two openings 28, 29 of the bores 26 no longer overlap.

In order that, in the open position of the fluid channel, the liquid passes only through the bore 26 and not between the cone surface 27 and the wall of the interior space of the housing 18 or in order that the stopcock 11, in the closed position, is actually also fluid-tight, the cone surface 27 has webs 30, 31, 32. In the exemplary embodiment illustrated here, the cone surface 27 is assigned above and below the bore 26 in each case one annular, horizontal web 30, 31. Owing to the cone shape, the upper web 30 has a larger diameter than the lower web 31. In the exemplary embodiment illustrated in FIGS. 3-5 of the plug 19, these two webs 30, 31 are assigned four vertical webs 32. The ends of the vertical webs 32 extend to the horizontal webs 30, 31, so that the webs 30, 31, 32 have a common sealing surface 33. Said sealing surface 33 is formed in such a way that it coincides with the inner wall of the housing 18 and thereby forms a sealing action. In order that said seal meets even the highest requirements, it is necessary for the webs 30, 31, 32 or the sealing surface 33 to be produced with a high degree of precision. Furthermore, for sufficient stability, the webs 30, 31, 32 must have a high hardness. According to the invention, this is achieved in that the plug 19 is produced in one part by means of an injection-moulding process and is embossed directly after the injection moulding. Here, it is in particular the case that the webs 30, 31, 32 of the cone part 20 are embossed in such a way that they acquire the corresponding degree of precision and material hardness. Due to the fact that the embossing is carried out directly after the injection moulding, that is to say still within the injection-moulding apparatus, the production of the plug 19 is realized in a single step. The method according to the invention dispenses in particular with the removal of the injection-moulded plug 19 and the renewed clamping in an embossing apparatus. This combination of the injection moulding and the embossing thus allows the plug 19 to be produced very easily, quickly and inexpensively. Here, it is even possible for a multiplicity of the plugs 19 described here to be produced at the same time.

Figure 4:
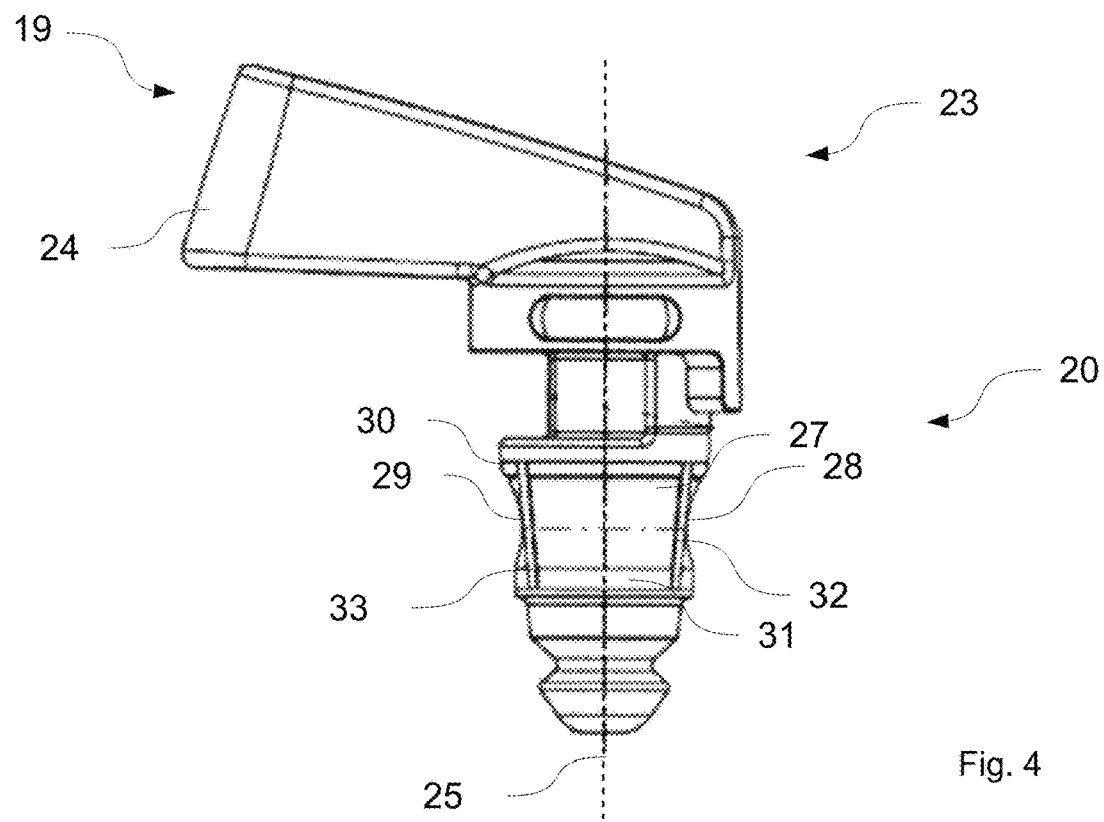
FIG. 4 shows a further illustration of the plug as per FIG. 3.
Figure 5:
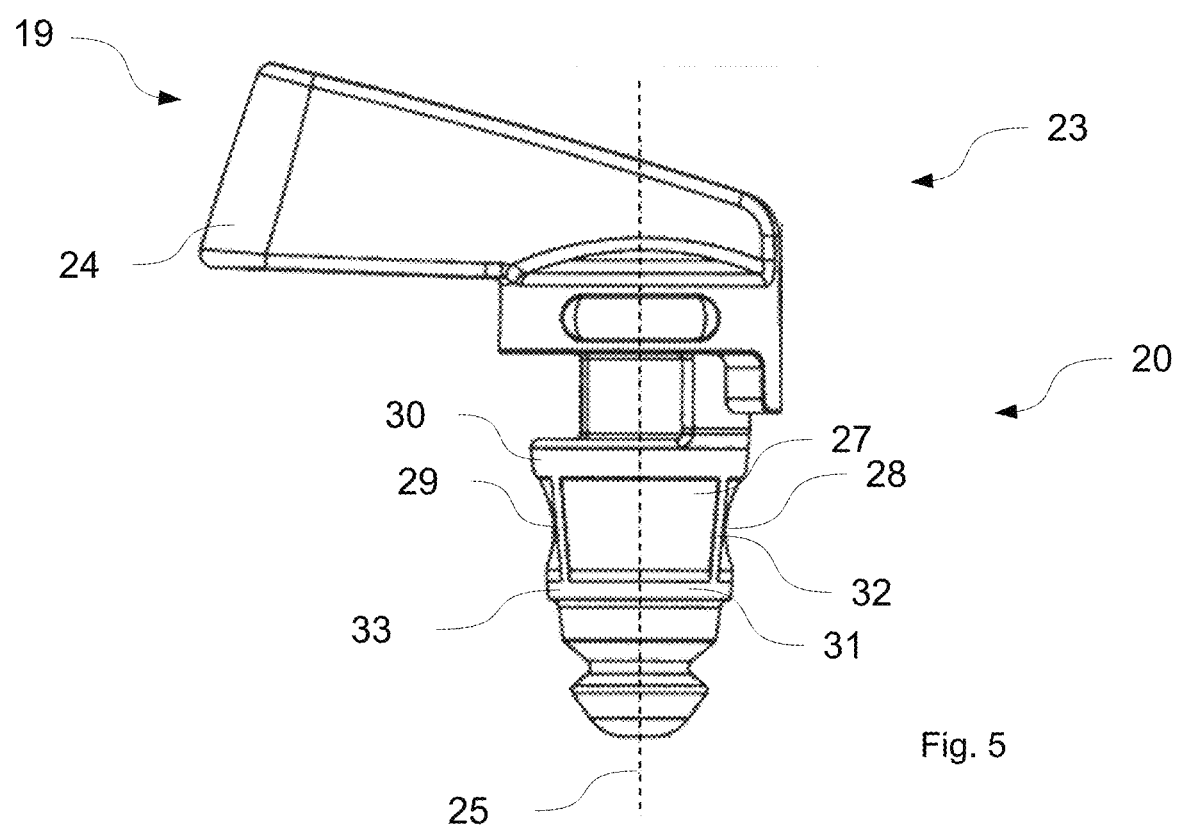
FIG. 5 shows an illustration of the plug as per FIG. 4 after an embossing process.

During the embossing process, all the webs 30, 31, 32 may be embossed to the same extent, as illustrated in FIGS. 4 and 5. FIG. 4 shows a plug 19 after the injection-moulding process. In the directly following embossing process, the horizontal webs 30, 31 are embossed in such a way that they form a planar sealing surface 33 with the webs 32 (FIG. 5). During this embossing process, the vertical webs 32 may also be shaped. Ultimately, the webs 30, 31, 32 are embossed in such a way that a highly-precise sealing surface 33 with respect to the plug 19 is formed.

This multi-dimensional embossing subsequent to the injection-moulding process can be carried out particularly well for PEEK. However, use may also be made of other plastics which have a similar material property. Ultimately, it is likewise conceivable for further components of the stopcock 11 or of the hand-held medical instrument to be produced in the manner described here.

Figure 3:
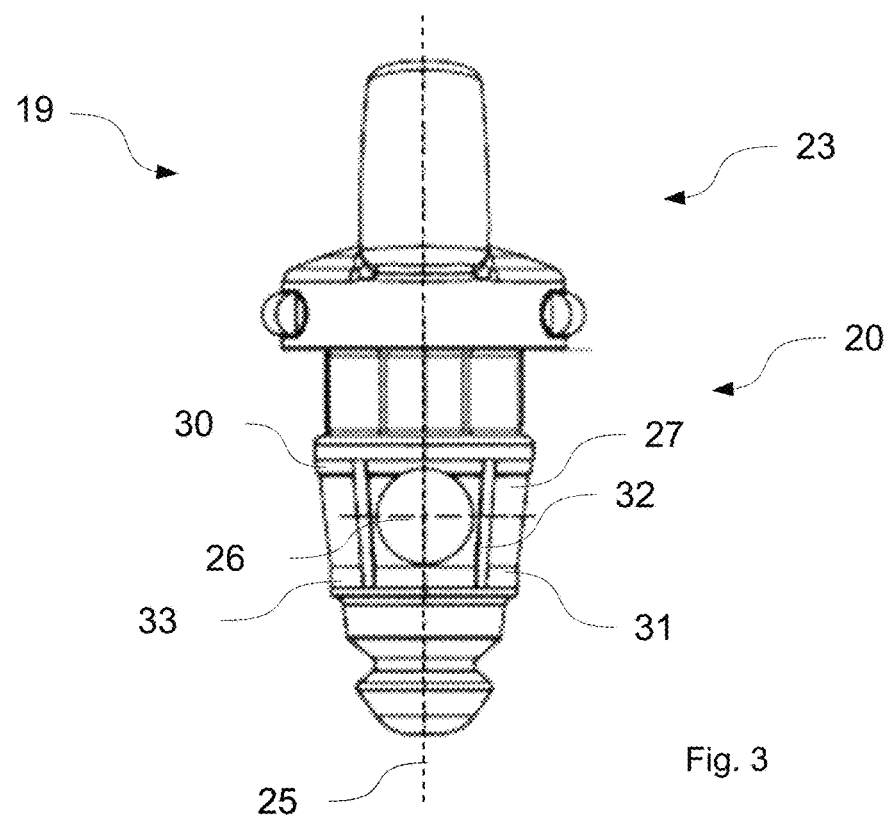
FIG. 3 shows an illustration of a plug.

The further features, visible in FIGS. 3-5, of the plug 19 will not be discussed any further here since they are not relevant to the present invention. For a more detailed description in this respect, reference is made to the specified prior art.

LIST OF REFERENCE SIGNS

10 Endoscope
11 Stopcock
12 Shaft part
13 Main body
14 Inlet connector
15 Eyepiece
16 Grip piece
17 Grip piece
18 Housing
19 Plug
20 Cone part
21 Connection part
22 Connection part
23 Grip
24 Grip part
25 Axis of rotation
26 Bore
27 Cone surface
28 Opening
29 Opening
30 Horizontal web
31 Horizontal web
32 Vertical web
33 Sealing surface

The invention claimed is:

1. A plug for a stopcock for producing and breaking a fluidic connection between at least two connection parts, the plug configured to be mounted in a rotatable manner in an interior space of a housing of the stopcock and includes: a cone part that has a cone surface, and a grip part that has a grip, wherein:
the cone part has a cylindrical bore having a longitudinal axis that is perpendicular to an axis of rotation,
the cone surface has horizontal webs and vertical webs which are configured to be brought into a sealing connection with an inner surface of the interior space of the housing, wherein the plug, with the cone part and the grip part, is formed in one part,
the cone surface has at least two horizontal webs that extend annularly around the cone part,
one horizontal web is arranged above the cylindrical bore and one horizontal web is arranged below the cylindrical bore,
the cone surface has at least four vertical webs that extend adjacent to outlet openings of the cylindrical bore along the cone surface,
the webs are straight or curved,
the vertical webs have a width which corresponds at least to a diameter of the cylindrical bore,
the vertical webs extend, in each case adjacent to the outlet openings of the cylindrical bore, along the cone surface, and the vertical webs are arranged in a semi-circle around the cylindrical bore,
ends of the vertical webs each coincide with one of the at least two horizontal webs, and
the cylindrical bore overlaps at least one of the horizontal webs along a direction parallel to the longitudinal axis of the cylindrical bore.

2. The plug for a stopcock according to claim 1, wherein the cone part, the grip part and the webs are produced in one part from the same material.

3. The plug for a stopcock according to claim 1, wherein the form of the vertical webs has a particularly high degree of precision as a result of an embossing process.

4. A stopcock for producing and breaking a fluidic connection between at least two connection parts having a plug according to claim 1.

5. A method for producing a plug for a stopcock for producing and breaking a fluidic connection between at least two connection parts,
wherein the plug is configured to be mounted in a rotatable manner in an interior space of a housing of the stopcock and includes a cone part, which has a cone surface, and a grip part, which has a grip, wherein the cone part has a cylindrical bore that has a longitudinal axis that is perpendicular to the axis of rotation, wherein the cone surface has horizontal and vertical webs which are configured to be brought into sealing connection with an inner surface of the interior space of the housing according to claim 1, wherein the plug, with the cone part and the grip part, is produced in one part, wherein the vertical webs extend, in each case adjacent to the outlet openings of the cylindrical bore, along the cone surface, and the vertical webs are arranged in a semi-circle around the cylindrical bore, wherein ends of the vertical webs each coincide with one of the at least two horizontal webs, wherein the plug, with the cone part and the grip part, is injection-moulded in one part and is embossed in a directly following process, wherein, as a result of the embossing, the cone surface and/or the webs acquire(s) a required degree of precision, wherein the injection moulding of the plug and the embossing of the webs are realized in a common process step, and the injection-moulded plug is embossed in an injection-moulding apparatus, and wherein the cylindrical bore overlaps at least one of the at least two horizontal webs along a direction parallel to a longitudinal axis of the cylindrical bore.

6. The method for producing a plug according to claim 5, wherein the webs are flattened by the embossing, wherein the webs acquire the required degree of precision as a result of compression.

7. The plug for a stopcock according to claim 1, wherein the outlet openings of the cylindrical bore are congruent with cylindrical connection parts.

8. The plug for a stopcock according to claim 1, wherein the width of the vertical webs extends in a direction traverse to the axis of rotation and the width of the vertical webs is equal to at least to the diameter of the cylindrical bore.

* * * * *